(12) United States Patent
Garland et al.

(10) Patent No.: US 6,244,507 B1
(45) Date of Patent: Jun. 12, 2001

(54) AUTOMATIC GRID PARAMETER LOGGING FOR DIGITAL RADIOGRAPHY

(75) Inventors: Harry T. Garland, Los Altos Hills; David D. Deer, Mountain View, both of CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/344,214

(22) Filed: Jun. 25, 1999

(51) Int. Cl.$^7$ ............................. G03B 42/04; G06K 15/00
(52) U.S. Cl. .......................... 235/383; 235/385; 378/154; 378/162; 378/210
(58) Field of Search ..................................... 235/383, 385, 235/375; 378/162, 210, 154

(56) References Cited

U.S. PATENT DOCUMENTS

| | | | |
|---|---|---|---|
| 5,757,021 | * | 5/1998 | Dewaele ................................ 250/581 |
| 6,032,856 | * | 3/2000 | Bischoff et al. ...................... 235/375 |
| 6,080,992 | * | 6/2000 | Nonaka et al. ....................... 378/147 |

OTHER PUBLICATIONS

Canon U.S.A., Inc., advertisement for Canon Digital Radiography System, 1997, Lake Success, NY.
Bushong, Stewart C., "Radiologic Science for Technologist" Chapter 18, pp 214–228, 1997, St. Louis, MO.
Yamazaki, Tatsuya, et al., "Development of Digital Radiography System," Computer Assisted Radiology and Surgery, Proceedings of the 12$^{th}$ International Symposium and Exhibition, Tokyo, Japan, Jun. 24–27, 1998, pp. 536–541.
Kameshima, Toshio, et al., "Novel Large Area MIS–type X–ray Image Sensor for Digital Radiography," Part of the SPIE Conference on Physics of Medical Imaging, pp. 453–462, Feb. 1998, San Diego, CA.

"Digital Imaging and Communications in Medicine (DICOM) Supplement 32: Digital X–Ray Supplement", Sep. 1, 1998, American Dental Association, Chicago, IL.

* cited by examiner

*Primary Examiner*—Robert H. Kim
*Assistant Examiner*—Drew A. Dunn
(74) *Attorney, Agent, or Firm*—Fenwick & West LLP

(57) ABSTRACT

A method, computer program product, and digital radiography system (100) detect type information concerning an anti-scatter grid (107), and store the information in a header (129) of a file (127) containing a digital x-ray image. A gleaning module (101) gleans relevant information from an identifier (103) on a physical medium (105) containing the anti-scatter grid (107). A retrieval module (121) retrieves an entry (123) corresponding to information gleaned from the identifier (103) and containing information concerning the anti-scatter grid (107) from a look-up table (119) in a computer memory (115). A storage module (131) stores the information in a header (129) of a file (127) containing the digital x-ray image. Additionally, a comparison module (401) compares type information concerning the identified anti-scatter grid (107) with type information for a correct anti-scatter grid for a procedure being performed. When the anti-scatter grid (107) being used is incorrect for the procedure, an alerting module (403) alerts an operator of the digital radiography system (100) of the error.

19 Claims, 5 Drawing Sheets

AUTOMATIC GRID PARAMETER LOGGING FOR DIGITAL RADIOGRAPHY

TECHNICAL FIELD

This invention pertains to the identification of an x-ray anti-scatter grid in a digital radiography system.

BACKGROUND ART

In a digital radiography system, an x-ray image is captured by a digital sensor plate. Usually, the captured image is stored in a digital file in a computer system. When the image is stored in a digital file, information corresponding to the x-ray image can be stored in a header of the file. Information corresponding to the x-ray image could include, for example, the date the image was created, the patient's name, the patient's age, the physician's name, and hardware specifications of the digital radiography system.

The Digital Imaging and Communications in Medicine (DICOM) standards committee has published technical standards related to digital radiography (DICOM Supplement 32: Digital X-ray Supplement). This DICOM Supplement defines a standard for what information is to be included in the header of a file containing a digital x-ray image. According to this standard, the file header may include technical parameters of an anti-scatter grid used in a digital radiography system while capturing an x-ray image.

An anti-scatter grid is a physical device that blocks scattered radiation. When a primary x-ray beam interacts with a body, secondary x-rays are scattered in all directions. Secondary x-rays that are traveling in a direction other than that of the primary beam cause a radiographic fog in the x-ray image. Such radiographic fog reduces the contrast of the image.

An anti-scatter grid is comprised of alternating sections of radiopaque material (typically lead) and radiolucent material (typically aluminum), encased in a protective, radiolucent housing. An anti-scatter grid is designed to absorb only the x-rays traveling in a direction other than that of the primary beam.

Various technical parameters of an anti-scatter grid determine its effectiveness under different conditions. An anti-scatter grid may be parallel or focused. In a parallel grid, all of the radiopaque sections are parallel to each other, and perpendicular to the surface of the grid. In a focused grid, the radiopaque sections are progressively tilted such that straight lines extended from the points at which the sections intersect with the surface of the grid would intersect at a single point. This point is defined as the focal point of the grid. Parallel grids are less expensive to manufacture than focused grids, but have the undesirable effect of absorbing more of the primary x-rays. Focused grids absorb less primary radiation, but unlike parallel grids must be used at an appropriate focal distance from the beam source, plus or minus an acceptable margin of error.

Both parallel and focused grids may be linear or crossed. A linear grid is comprised of a single parallel or focused anti-scatter grid. A crossed grid is comprised of two linear grids, one on top of the other, such that the radiopaque sections of one grid are perpendicular to those of the other. Crossed grids absorb a significantly higher percentage of the scattered radiation than linear grids, but must be positioned much more carefully relative to the source of the x-ray beam. All grids may also be fixed in position, or moving. Moving grids are attached to a mechanism that is moved as the x-rays pass through the body being radiographed. This has the effect of minimizing, in the x-ray image, lines caused by the absorbence of primary x-rays by the grid.

Other technical parameters of the grid are the specific radiopaque and radiolucent materials used, the width of the sections of radiopaque material, the width of the sections of radiolucent material, the height of the grid, the ratio of the height of the grid to the width of the sections of radiopaque material (called the grid aspect ratio), the focal distance of the grid (relevant for focused grids only), and the period of time for which the grid is in motion while the digital sensor plate is being exposed to radiation (relevant for moving grids only). All of these factors determine the extent to which a grid will absorb secondary radiation, the extent to which a grid will undesirably absorb primary radiation, the proper range of focal distances for the grid, the tolerance of the grid for use outside of that range, and the dose of radiation to which the body being radiographed must be exposed in order to generate a useful x-ray image.

The DICOM standard specifies that the header of the file containing a digital x-ray image may contain various technical information concerning the grid that was used in the generation of the image. Such information comprises the type of the grid (e.g. focused, parallel, crossed, linear), the radiopaque material (e.g. lead, uranium), the radiolucent material (e.g. aluminum, plastic), the width of the radiopaque material in millimeters, the pitch of the radiopaque material in millimeters, the grid aspect ratio, the grid focal distance, and the period in milliseconds for which the grid moves during image generation (relevant for moving grids only).

It is useful to have a record of this information for multiple reasons. First, a record of the grid used in a specific x-ray procedure aids future medical research by providing data on the conditions of a past medical examination, the results of which are known. Second, it provides documentation that the correct grid for a specific procedure was utilized. Because different medical procedures require different focal distances and doses of radiation, different anti-scatter grids are best suited for different procedures. It is beneficial to health care providers to maintain a record that the correct grids were used for various procedures.

Presently, most radiography is executed using film. Thus, no digital file is created in which to store information concerning the examination. Instead, the radiography technician generally writes information concerning the examination on the film jacket in which the film is stored. Such information may or may not include the anti-scatter grid type. Because the process is entirely manual, it is highly subject to error and omission.

In an existing digital radiography system, a technician may manually enter information concerning the examination into a computer system for storage in the header of a digital file. Again, such information may or may not include the grid type, and is highly subject to error and omission. The technician may neglect to enter relevant information, the technician may make a typographical error, and the technician may be unaware of or mistaken concerning the detailed technical parameters of the anti-scatter grid that was utilized in the procedure. Manual entry of such information is also time-consuming.

Furthermore, it is possible for the technician to use the wrong anti-scatter grid during a procedure and not become aware of this mistake until viewing the resulting x-ray image. Such a mistake would be preventable if the digital radiography system were able to detect the use of an incorrect anti-scatter grid for the procedure being performed, and to alert the technician of the error.

What is needed is a way for a digital radiography system to identify an anti-scatter grid and its technical parameters, and to automatically store that information in the header of the file containing the digital x-ray image. Additionally, a way is needed for a digital radiography system to automatically detect when an anti-scatter grid being used is not the correct grid for the procedure being performed, and to alert the technician of the error.

DISCLOSURE OF INVENTION

The present invention is a method, computer program product, and digital radiography system (100) for detecting type information concerning an anti-scatter grid (107). Relevant information is gleaned from an identifier (103) on a physical medium (105) containing an anti-scatter grid (107). A look-up table (119) containing known possible anti-scatter grid types is accessed from a computer memory (115). An entry (123) corresponding to information gleaned from the identifier (103) and containing information concerning the anti-scatter grid (107) is retrieved from the look-up table (119).

BRIEF DESCRIPTION OF THE DRAWINGS

These and other more detailed and specific objects and features of the present invention are more fully disclosed in the following specification, reference being had to the accompanying drawings, in which.

DETAILED DESCRIPTION OF THE PREFERRED EMBODIMENTS

Figure 1:
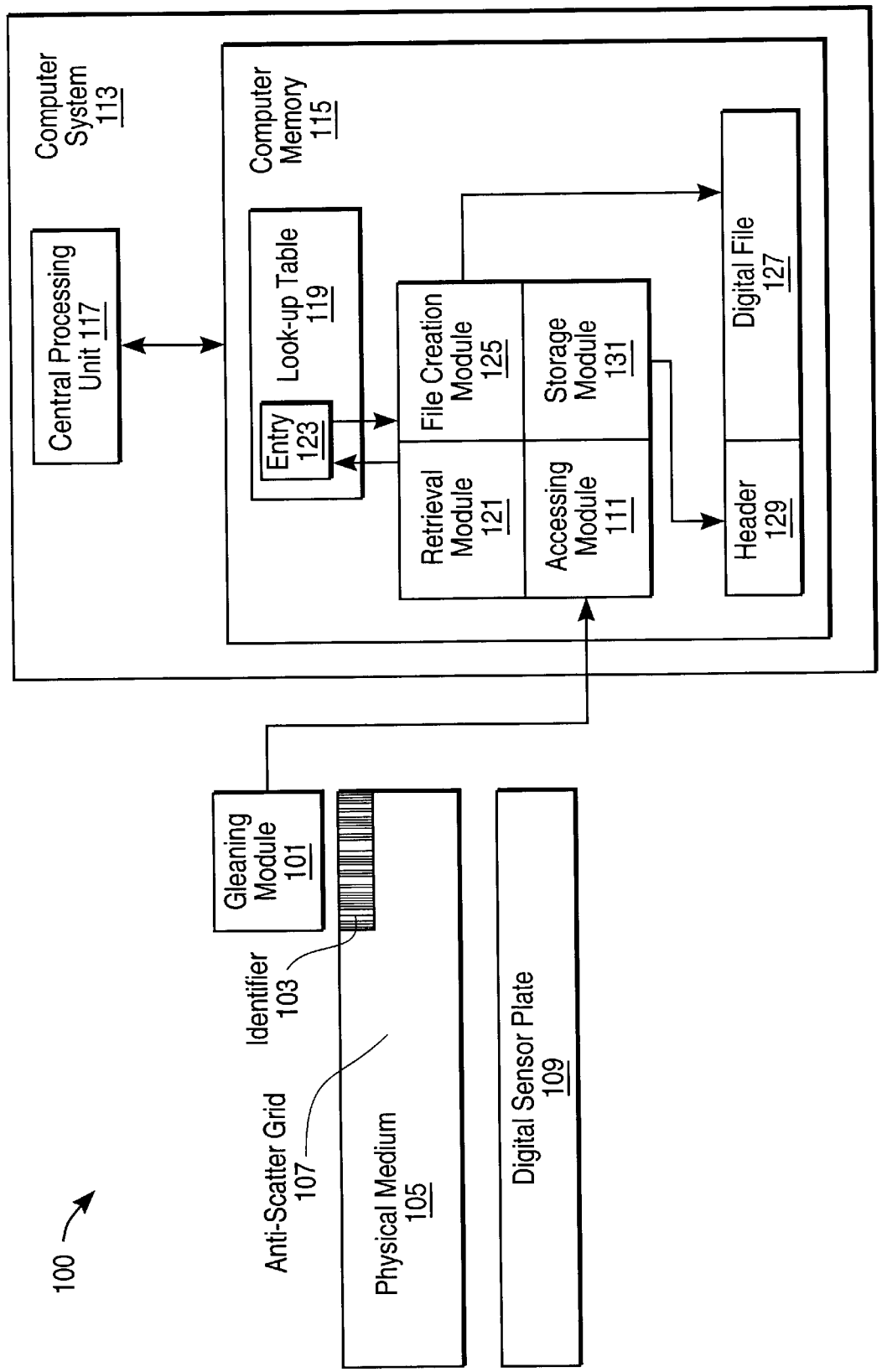
FIG. 1 is a high level block diagram illustrating a preferred embodiment of the present invention for detecting and storing type information concerning an anti-scatter grid in a digital radiography system.

FIG. 1 is a high level block diagram illustrating an overview of a preferred embodiment of the present invention for detecting and storing type information concerning an anti-scatter grid in a digital radiography system 100. A gleaning module 101 gleans relevant information from an identifier 103 on a physical medium 105 containing an anti-scatter grid 107. The anti-scatter grid 107 is positioned above a digital sensor plate 109. In a preferred embodiment of the present invention, the gleaning module 101 is comprised of an optical-electrical apparatus and software to control it. In alternative embodiments, the gleaning module 101 may be implemented in various combinations of hardware plus software and/or firmware as desired.

Figure 2:
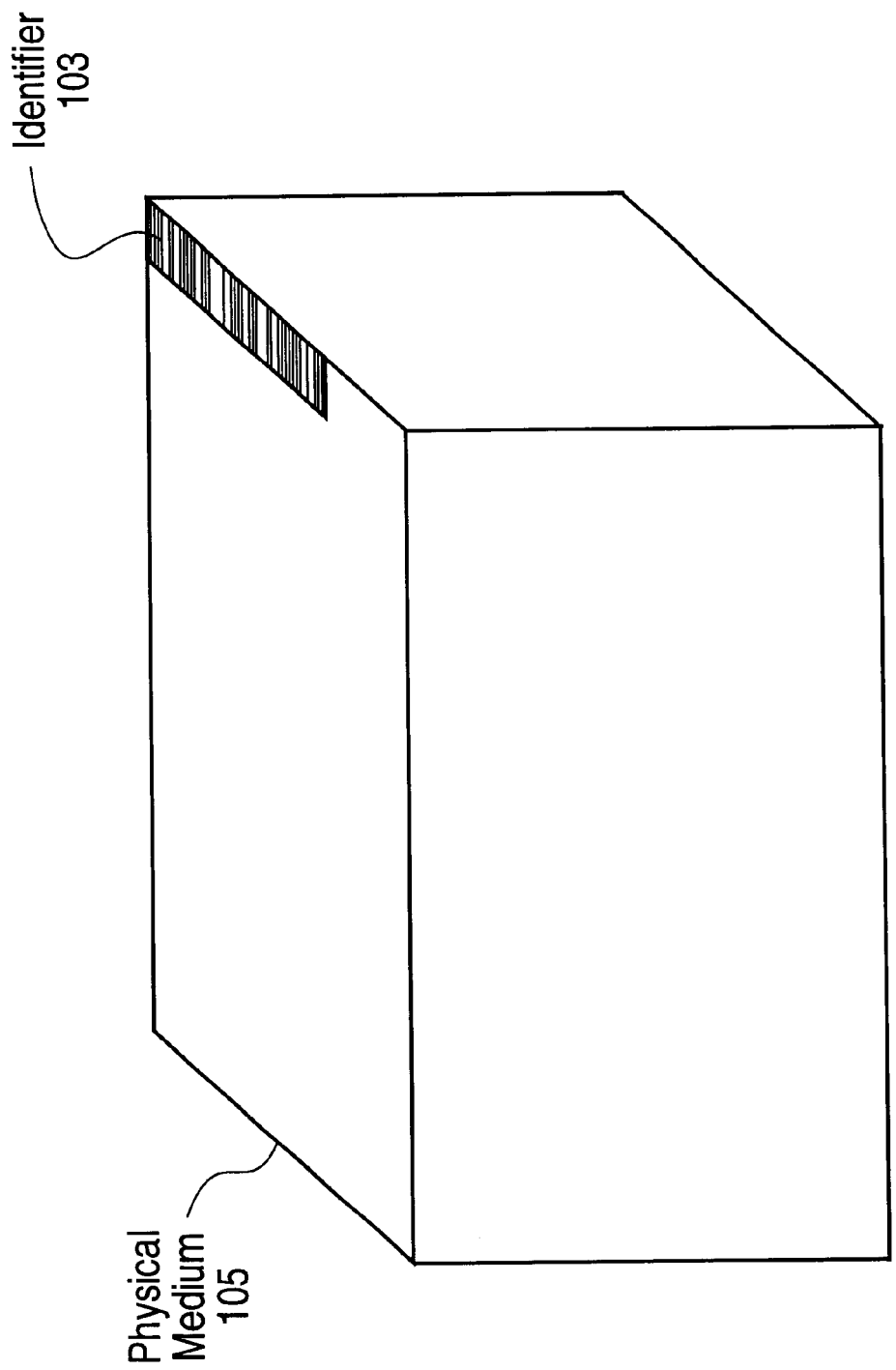
FIG. 2 is a block diagram illustrating an identifier on a surface of a physical medium containing an anti-scatter grid in a preferred embodiment of the present invention.

FIG. 2 illustrates in greater detail the identifier 103 on the physical medium 105 containing the anti-scatter grid 107 in a preferred embodiment of the present invention. The identifier 103 is comprised of a series of physical notches, uniformly varying from the embedding medium. Each notch represents a bit with a value of 0 or 1, such that the series of notches represents a numerical value unique to the grid on which it is embossed. The gleaning module 101 preferably gleans this unique numerical value. In alternative embodiments of the present invention, other types of identifiers are utilized as desired, such as a magnetic strip, for example a bar code or a printed or silk screened pattern.

Returning to FIG. 1, an accessing module 111 is coupled to the gleaning module 101. The accessing module 111 is preferably in a computer system 113 having a computer memory 115 and a central processing unit 117. The accessing module 111 accesses a look-up table 119 containing information concerning known anti-scatter grid types. In a preferred embodiment of the present invention, the accessing module 111 is comprised of software residing in the computer memory 115 of the computer system 113. In various embodiments of the present invention, the accessing module 111 may be implemented as software, hardware, firmware, or various combinations of the three as desired.

In a preferred embodiment of the present invention, the look-up table 119 is stored in the computer memory 115 of the computer system 113. In an alternative embodiment, the look-up table 119 is stored in a computer memory at a location physically remote from the digital radiography system, and is accessed through conventional communications means. In other alternative embodiments of the present invention, the look-up table is stored in alternative computer readable memories, such as a read only memory circuit or a flash memory, as desired.

A retrieval module 121, coupled to the accessing module 111, retrieves an entry 123 corresponding to information gleaned from the identifier 103 and containing information concerning the anti-scatter grid 107 from the look-up table 119. In a preferred embodiment of the present invention, the retrieval module 121 is comprised of software residing in the computer memory 115 of the computer system 113. In various embodiments of the present invention, the retrieval module 121 may be implemented as software, hardware, firmware, or various combinations of the three as desired.

A file creation module 125 creates a digital file 127 containing a digital x-ray image and a file header 129. The file creation module 125 preferably creates the file 127 in the computer memory 115 of the computer system 113. In alternative embodiments, the file creation module 125 creates the file 127 on various types of computer writeable media as desired. In a preferred embodiment of the present invention, the file creation module 125 is comprised of software residing in the computer memory 115 of the computer system 113. In various embodiments of the present invention, the file creation module 125 may be implemented as software, hardware, firmware, or various combinations of the three as desired.

A storage module 131, coupled to the file creation module 125, stores the information concerning the anti-scatter grid 107 in the header 129 of the digital file 127 in the computer memory 115 of the computer system 113. In various embodiments of the present invention, the storage module 131 proceeds to store the file 127 on different formats of computer writeable media, such as a hard disk or an optical disk, as desired. In all embodiments, the information is stored to be exploited at a later time. In a preferred embodiment of the present invention, the storage module 131 is comprised of software residing in the computer memory 115 of the computer system 113. In various embodiments of the present invention, the storage module 131 may be implemented as software, hardware, firmware, or various combinations of the three as desired.

Figure 3:
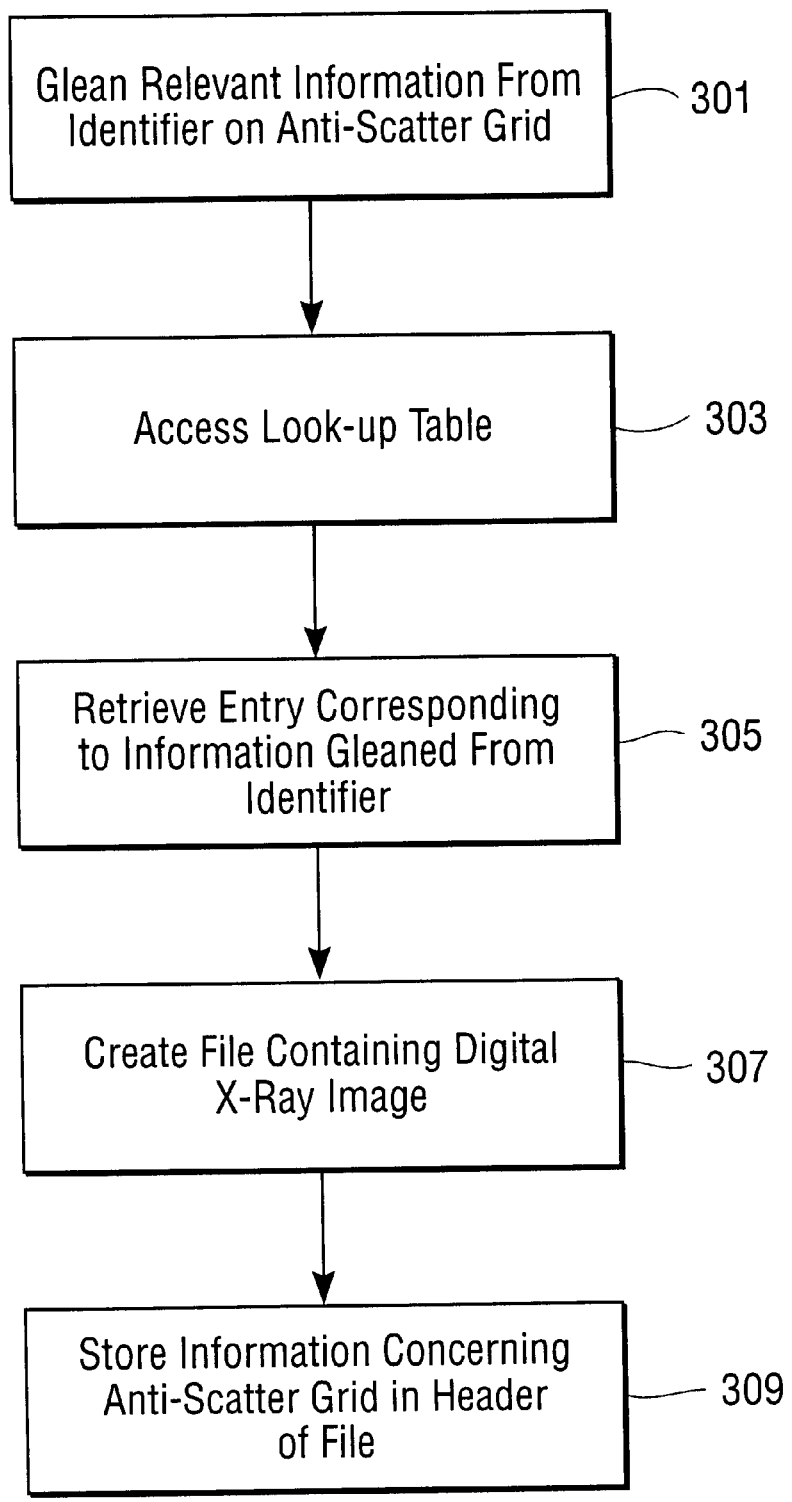
FIG. 3 is a high level flow chart illustrating the steps of gleaning relevant information from an identifier, accessing a look-up table, retrieving an entry pertaining to the identifier, creating a file, and storing type information about an installed anti-scatter grid in the header of the file, as performed by a preferred embodiment of the present invention.

FIG. 3 is a high level flow chart illustrating the steps of gleaning, accessing, retrieving, and storing as performed by a preferred embodiment of the present invention. The gleaning module 101 gleans 301 relevant information from the identifier 103 on the physical medium 105 containing the anti-scatter grid 107. The accessing module 111 accesses 303 the look-up table 119 in the computer memory 115 of the computer system 113. The retrieval module 121 retrieves 305 the entry 123 corresponding to information gleaned from the identifier 103 and containing information about the anti-scatter grid 107 from the look-up table 119. The file creation module 125 creates 307 a file 127 containing a digital x-ray image and a file header 129. The storage module 131 stores 309 the information concerning the anti-scatter grid 107 in the header 129 of the file 127.

Figure 4:
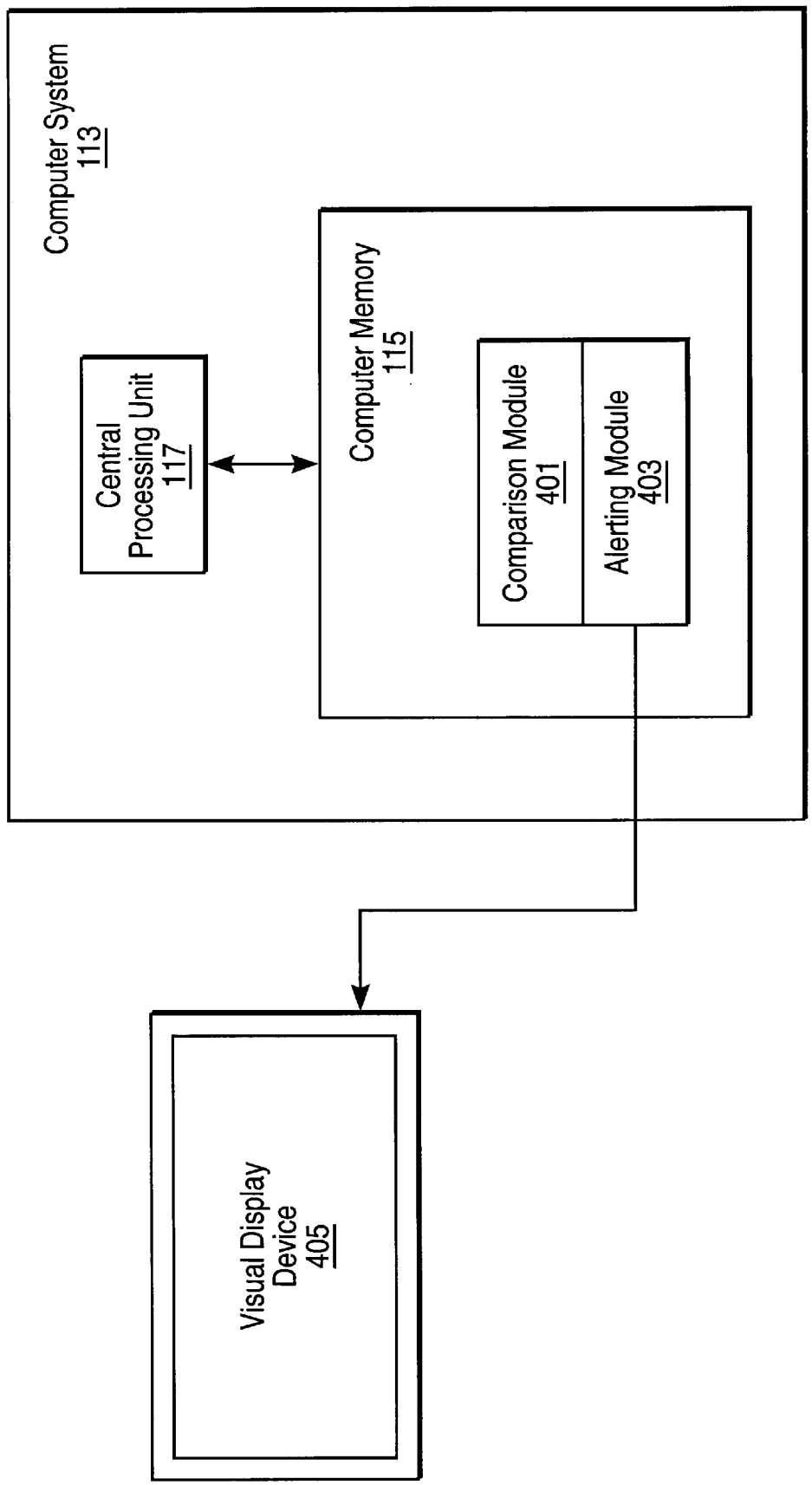
FIG. 4 is a block diagram illustrating the comparison of information concerning an installed anti-scatter grid with information for a correct anti-scatter grid for a procedure being performed, and the subsequent alerting of a system operator when an incorrect anti-scatter grid is being used, in a preferred embodiment of the present invention.

FIG. 4 illustrates the comparison of information concerning an installed anti-scatter grid 107 with information for a correct anti-scatter grid for a procedure being performed, and the subsequent alerting of an operator when an incorrect grid is being used. A comparison module 401 compares the type information for the installed anti-scatter grid 107 with type information for the correct anti-scatter grid for the procedure being performed. In a preferred embodiment of the present invention, the comparison module 401 is comprised of software residing in the computer memory 115 of the computer system 113. In various embodiments of the present invention, the comparison module 401 may be implemented as software, hardware, firmware, or various combinations of the three as desired.

When an incorrect anti-scatter grid is being used, an alerting module 403, preferably coupled to the comparison module 405, alerts an operator of the digital radiography system as to the error. In a preferred embodiment of the present invention, the alerting module 403 alerts the operator by displaying a message on a visual display device 405. In alternative embodiments, the alerting module 403 alerts the operator in other ways, such as by generating an aural alarm tone on a speaker. In a preferred embodiment of the present invention, the alerting module 403 is comprised of software residing in the computer memory 115 of the computer system 113. In various embodiments of the present invention, the alerting module 403 may be implemented as software, hardware, firmware, or various combinations of the three as desired.

Figure 5:
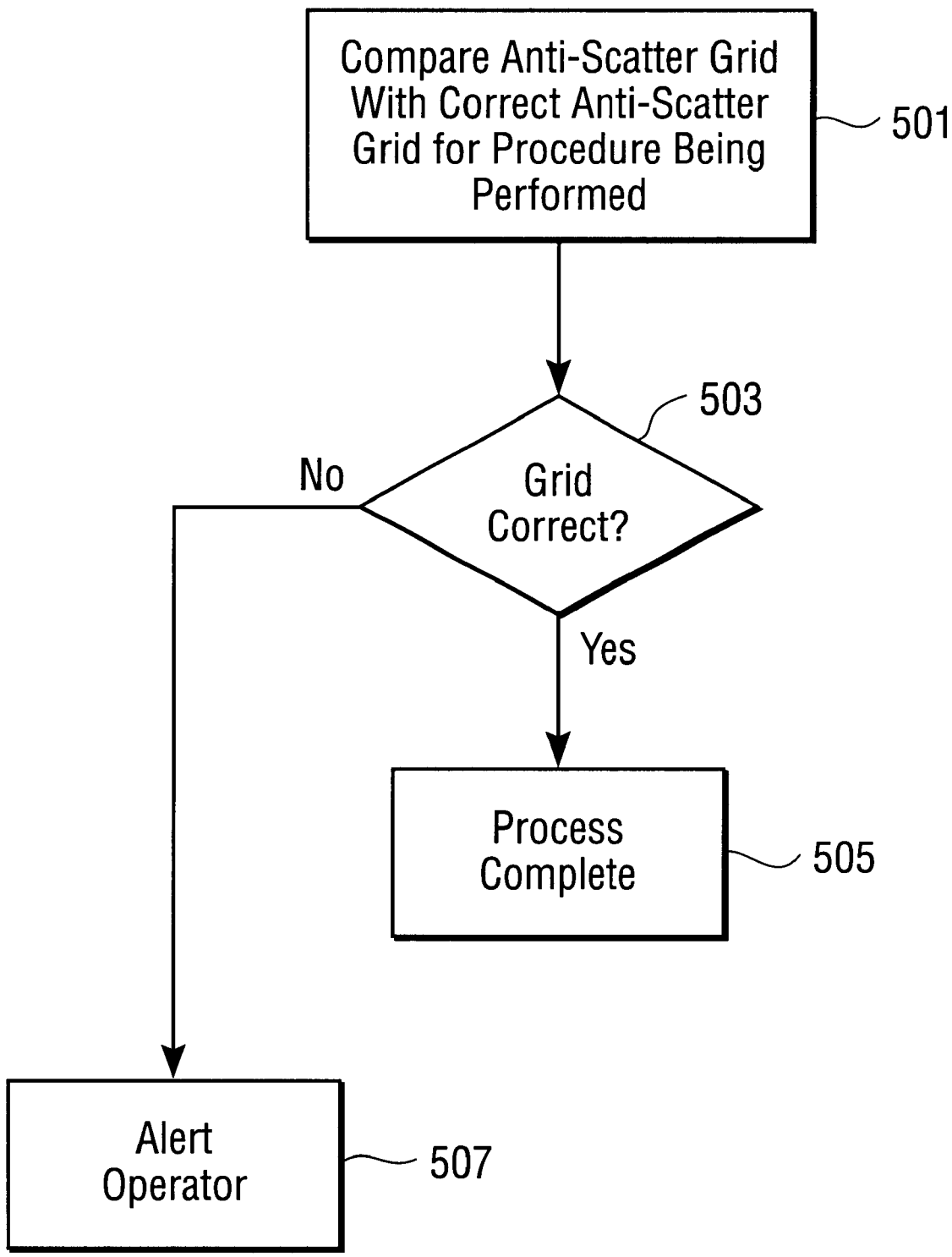
FIG. 5 is a flow chart illustrating the steps, as performed in a preferred embodiment of the present invention, of comparing information concerning an installed anti-scatter grid with information for a correct anti-scatter grid for a procedure being performed, and alerting a system operator as to the error when an incorrect anti-scatter grid is being used.

FIG. 5 is a flowchart illustrating the steps involved in the above described comparing and alerting. The comparison module 401 compares 501 the type information for the installed anti-scatter grid 107 with the type information for the correct anti-scatter grid for the procedure being performed. By so comparing 501, the comparison module 401 determines 503 if the anti-scatter grid 107 is the correct one for the procedure. If it is, the comparing and altering process is complete 505. If the grid being used is incorrect for the procedure, the alerting module 403 alerts 507 the operator of the digital radiography system of the error.

In an alternative embodiment of the present invention, a display module displays information concerning the anti-scatter grid 107 to an operator of the digital radiography system.

In another alternative embodiment of the present invention, the anti-scatter grid 107 is non-replaceable, and thus is always of the same type. In such an embodiment, the file creation module 125 creates a file 127 containing a digital x-ray image and a header 129, and the storage module 131 stores information concerning the anti-scatter grid 107, to be exploited at a later time, in the file header 129.

The above description is included to illustrate the operation of the preferred embodiments and is not meant to limit the scope of the invention. The scope of the invention is to be limited only by the following claims. From the above discussion, many variations will be apparent to one skilled in the art that would yet be encompassed by the spirit and scope of the present invention.

What is claimed is:

1. In a digital radiography system, a method for detecting type information concerning an anti-scatter grid, the method comprising:

gleaning relevant information from an identifier on a physical medium containing the anti-scatter grid;

accessing a look-up table in a computer memory, the look-up table containing known possible anti-scatter grid types;

retrieving an entry corresponding to relevant information gleaned from the identifier and containing information concerning the anti-scatter grid from the look-up table;

creating a digital file containing a digital x-ray image, the digital x-ray image having been created by utilizing the anti-scatter grid; and storing information concerning the anti-scatter grid in a header of the digital file.

2. The method of claim 1, wherein the identifier consists of a series of notches varying from surrounding medium, each notch being interpreted as a bit with a state of 0 or 1.

3. The method of claim 1, wherein the look-up table is stored in a computer memory at a location physically remote from the digital radiography system, the computer memory being accessible to the digital radiography system through conventional communications means.

4. The method of claim 1, wherein the digital radiography system displays the information concerning the anti-scatter grid to an operator.

5. In a digital radiography system including a non-replaceable anti-scatter grid, a method for storing type information, said method comprising:

creating a digital file containing a digital x-ray image, the digital x-ray image having been created by utilizing the anti-scatter grid; and storing information concerning the anti-scatter grid in a header of the digital file.

6. A computer readable medium containing a computer program product for detecting type information concerning an anti-scatter grid in a digital radiography system, the computer program product comprising:

program code for gleaning relevant information from an identifier on a physical medium containing the anti-scatter grid;

program code for accessing a look-up table in a computer memory, the look-up table containing known possible anti-scatter grid types;

program code for retrieving an entry corresponding to relevant information gleaned from the identifier and containing information concerning the anti-scatter grid from the look-up table;

program code for creating a digital file containing a digital x-ray image, the digital x-ray image having been created by utilizing the anti-scatter grid; and program code for storing information concerning the anti-scatter grid in a header of the digital file.

7. The computer readable medium of claim 6, wherein the computer program product comprises program code for displaying information concerning the anti-scatter grid to an operator of the digital radiography system.

8. A computer readable medium containing a computer program product for storing type information concerning a non-replaceable anti-scatter grid in a digital radiography system, the computer program product comprising:
 program code for creating a digital file containing a digital x-ray image, the digital x-ray image having been created by utilizing the anti-scatter grid; and
 program code for storing information concerning the anti-scatter grid in a header of the digital file.

9. A digital radiography system for detecting type information concerning an anti-scatter grid, the system comprising:
 a gleaning module for gleaning relevant information from an identifier on a physical medium containing the anti-scatter grid;
 an accessing module, coupled to the gleaning module, for accessing a look-up table in a computer memory, the look up table containing known possible anti-scatter grid types;
 a retrieval module, coupled to the accessing module, for retrieving an entry corresponding to relevant information gleaned from the identifier and containing information concerning the anti-scatter grid from the look-up table;
 a file creation module for creating a digital file containing a digital x-ray image, the digital x-ray image having been created by utilizing the anti-scatter grid; and
 a storage module, coupled to the file creation module, for storing information concerning the anti-scatter grid in a header of the digital file.

10. The system of claim 9, further comprising a display module for displaying information concerning the anti-scatter grid to an operator of the digital radiography system.

11. A digital radiography system for storing type information concerning a non-replaceable anti-scatter grid, the system comprising:
 a file creation module for creating a digital file containing a digital x-ray image, the digital x-ray image having been created by utilizing the anti-scatter grid; and
 a storage module, coupled to the file creation module, for storing information concerning the anti-scatter grid in a header of the digital file.

12. In a digital radiography system, a method for detecting type information concerning an anti-scatter grid, the method comprising:
 gleaning relevant information from an identifier on a physical medium containing the anti-scatter grid;
 accessing a look-up table in a computer memory, the look-up table containing known possible anti-scatter grid types;
 retrieving an entry corresponding to relevant information gleaned from the identifier and containing information concerning the anti-scatter grid from the look-up table;
 creating a digital file containing a digital x-ray image, the digital x-ray image having been created by utilizing the anti-scatter grid;
 storing information concerning the anti-scatter grid in a header of the digital file;
 comparing type information concerning the anti-scatter grid with type information for an appropriate anti-scatter grid for a procedure being performed; and
 alerting an operator when an inappropriate anti-scatter grid is being used.

13. The method of claim 12, wherein:
 the identifier comprises a series of notches varying from surrounding medium, each notch being interpreted as a bit with a state of 0 or 1.

14. The method of claim 12, wherein:
 the look-up table is stored in a computer memory at a location physically remote from the digital radiography system, the computer memory being accessible to the digital radiography system through conventional communications means.

15. The method of claim 12, wherein:
 the digital radiography system displays information concerning the anti-scatter grid to an operator.

16. A computer readable medium containing a computer program product for detecting type information concerning an anti-scatter grid in a digital radiography system, the computer program product comprising:
 program code for gleaning relevant information from an identifier on a physical medium containing the anti-scatter grid;
 program code for accessing a look-up table in a computer memory, the look-up table containing known possible anti-scatter grid types;
 program code for retrieving an entry corresponding to relevant information gleaned from the identifier and containing information concerning the anti-scatter grid from the look-up table;
 program code for creating a digital file containing a digital x-ray image, the digital x-ray image having been created by utilizing the anti-scatter grid;
 program code for storing information concerning the anti-scatter grid in a header of the digital file;
 program code for comparing type information concerning the anti-scatter grid with type information for an appropriate anti-scatter grid for a procedure being performed; and
 program code for alerting an operator of the digital radiography system when an inappropriate anti-scatter grid is being used.

17. The computer readable medium of claim 16, wherein:
 the computer program product comprises program code for displaying information concerning the anti-scatter grid to an operator of the digital radiography system.

18. A digital radiography system for detecting type information concerning an anti-scatter grid, the system comprising:
 a gleaning module for gleaning relevant information from an identifier on a physical medium containing the anti-scatter grid;
 an accessing module, coupled to the gleaning module, for accessing a look-up table in a computer memory, the look up table containing known possible anti-scatter grid types;
 a retrieval module, coupled to the accessing module, for retrieving an entry corresponding to relevant information gleaned from the identifier and containing information concerning the anti-scatter grid from the look-up table;
 a creation module, coupled to the retrieval module, for creating a digital file containing a digital x-ray image, the digital x-ray image having been created by utilizing the anti-scatter grid;

a storage module, coupled to the creation module, for storing information concerning the anti-scatter grid in a header of the digital file;

a comparison module, coupled to the storage module, for comparing type information concerning the anti-scatter grid with type information for an appropriate anti-scatter grid for a procedure being performed; and an alerting module, coupled to the comparison module, for alerting an operator of the digital radiography system when an inappropriate anti-scatter grid is being used.

19. The system of claim 18, further comprising:

a display module for displaying information concerning the anti-scatter grid to an operator of the digital radiography system.

* * * * *